United States Patent
Cook

(10) Patent No.: US 11,896,608 B1
(45) Date of Patent: Feb. 13, 2024

(54) ALCOHOL METABOLISM ACCELERATION COMPOSITION

(71) Applicant: Christina Rahm Cook, Brentwood, TN (US)

(72) Inventor: Christina Rahm Cook, Brentwood, TN (US)

(*) Notice: Subject to any disclaimer, the term of this patent is extended or adjusted under 35 U.S.C. 154(b) by 171 days.

(21) Appl. No.: 17/488,492

(22) Filed: Sep. 29, 2021

Related U.S. Application Data

(60) Provisional application No. 63/087,420, filed on Oct. 5, 2020.

(51) Int. Cl.
| | | |
|---|---|---|
| *A61K 33/06* | (2006.01) | |
| *A61K 31/593* | (2006.01) | |
| *A61K 36/8962* | (2006.01) | |
| *A61K 31/375* | (2006.01) | |
| *A61K 31/355* | (2006.01) | |
| *A61K 31/714* | (2006.01) | |

(52) U.S. Cl.
CPC ............ *A61K 33/06* (2013.01); *A61K 31/355* (2013.01); *A61K 31/375* (2013.01); *A61K 31/593* (2013.01); *A61K 31/714* (2013.01); *A61K 36/8962* (2013.01)

(58) Field of Classification Search
CPC .... A61K 33/06; A61K 31/355; A61K 31/375; A61K 31/593; A61K 31/714; A61K 36/8962
See application file for complete search history.

(56) References Cited

U.S. PATENT DOCUMENTS

| | | | | |
|---|---|---|---|---|
| 2002/0193355 A1* | 12/2002 | Meignant | ............. | A61K 9/0056 424/602 |
| 2019/0000930 A1* | 1/2019 | Holstein | ............ | A61K 31/7076 |

FOREIGN PATENT DOCUMENTS

| | | | | |
|---|---|---|---|---|
| WO | WO-2016070017 A1 * | 5/2016 | ............. | A23L 19/01 |

* cited by examiner

*Primary Examiner* — Blessing M Fubara
(74) *Attorney, Agent, or Firm* — Gulf Coast Intellectual Property Group

(57) ABSTRACT

The present invention is a composition for increasing alcohol metabolism wherein the composition of the present invention is provided in a food substance and a drink formula. The embodiments of the composition of the present invention are operable to increase the alcohol metabolism of a user and also assist the body in burning the carbohydrates and sugars associated with alcohol consumption. The base of the composition of the present invention includes hydrous sodium aluminosilicate. Several embodiments of the present invention are provided wherein these embodiments can include some of the Vitamin B complex as well as hemp protein powder, calcium carbonate and magnesium oxide. The compositions of the present invention further include use of orthosilicates, Vitamin E, calcium, wheat grass, resveratrol, turmeric and theanine. The compositions of the present invention are provided in both liquid and solid forms.

5 Claims, 2 Drawing Sheets

| | |
|---|---|
| Organic Hemp Protein Powder | 400mg |
| Rhodiola Extract | 215mg |
| Magnesium | 97mg |
| Vitamin B6 | 32mg |
| Vitamin B12 | 4mcg |
| Folic Acid | 380mcg |
| Vitamin D3 | 400UI |

| | |
|---|---|
| Silicon Dioxide | 200mg |
| Absorbic Acid | 115mg |
| Potassium Sorbate | 80mg |
| B12 | 1.80mg |
| D3 | 2.0mg |

Fig. 1

| | |
|---|---|
| Organic Hemp Protein Powder | 400mg |
| Rhodiola Extract | 215mg |
| Magnesium | 97mg |
| Vitamin B6 | 32mg |
| Vitamin B12 | 4mcg |
| Folic Acid | 380mcg |
| Vitamin D3 | 400UI |

Fig. 2

| | |
|---|---|
| Vitamin C | 500mg |
| Calcium Carbonate | 500mg |
| Magnesium Oxide | 100mg |
| Vitamin B Complex | 90mg |
| Garlic Powder | 300mg |
| Vitamin E Acetate | 10mg |

Fig. 3

ALCOHOL METABOLISM ACCELERATION COMPOSITION

PRIORITY UNDER 35 U.S.C Section 119(e) & 37 C.F.R. Section 1.78

This nonprovisional application claims priority based upon the following prior United States Provisional Patent Application entitled: Alcohol Metabolism Accelerating Composition, Application No.: 63/087,420 filed Oct. 5, 2020, in the name of Christina Cook, which is hereby incorporated by reference for all purposes.

FIELD OF THE INVENTION

The present invention relates generally to metabolic increasing materials, more specifically but not by way of limitation a composition for increasing alcohol metabolism wherein the present invention is provided in a food substance and a drink formula both containing the composition of the present invention.

BACKGROUND

Alcohol consumption in the United States as well as other countries has steadily increasing year by year. During the recent pandemic, alcohol sales reached record levels. About sixty six million adult drinkers consume about nine liters of pure alcohol per person of the drinking population annually. Excessive consumption of alcohol is known to cause alcoholic disorders accompanied by a decrease in glutathione in the liver and an increase in lipid peroxidation. It is desirable to reduce alcohol intake so as to reduce the negative health consequences thereof. However, moderate drinking may have some benefits in areas such as dissipating stress and making life enjoyable. Complete elimination of drinking is not always easy as changing routine drinking habits can be difficult. Studies have been conducted on compositions that promote alcohol metabolism for the purpose of avoiding hangovers such as hangovers and reducing the effects on the liver. For example, γ-aminobutyric acid and sesamin have been shown to increase the rate of alcohol metabolism. However, it is difficult to say that these alcohol metabolism promoters have a sufficient effect. An exploration of utilizing orthosilicates in combination or alone with vitamins and minerals may have an increased desired effect of improving the metabolism of alcohol. It has been found that and vitamins and minerals including the B vitamins—B1 (Thiamine), B2 (riboflavin), B6 and B12 (Cobalamin), vitamin E, Resveratrol, turmeric, Vitamin C, garlic, Calcium, wheat grass, and theanine has various effects such as suppression of anxiety induction, suppression of premenstrual syndrome and improvement of mental concentration. In addition, and vitamins and minerals including the B vitamins—B1 (Thiamine), B2 (riboflavin), B6 and B12 (Cobalamin), vitamin E, Resveratrol, turmeric, Vitamin C, garlic, Calcium, wheat grass, and theanine has been reported to have an inhibitory action on acetoaldehyde toxicity. The present invention has been made in view of the above circumstances, and an object of the present invention is to provide a composition for promoting alcohol metabolism containing various forms of orthosilicates and vitamins and minerals including the B vitamins—B1 (Thiamine), B2 (riboflavin), B6 and B12 (Cobalamin), vitamin E, Resveratrol, turmeric, Vitamin C, garlic, Calcium, wheat grass, and theanine, and a food and drink containing the composition.

The alcohol metabolism promoting composition of the present invention alleviates or reduces disorders, such as but not limited to hangover or alcoholic liver injury caused by ingestion of various alcoholic beverages. It can be used spontaneously or on a daily basis for the purpose of improvement. The alcohol metabolism promoting effect of the composition of the present invention is brought about by a decrease in blood alcohol concentration. Through ingestion of the composition of the present invention before, during, or after intake of an alcoholic beverage, the blood alcohol concentration based on the absorption of alcohol in the beverage into the body is reduced more quickly. As such, it is possible to alleviate or improve the disorder caused by the consumption of alcoholic beverages. The composition of the present invention can provided such that it is combined with a food or liquid. Examples of such foods and drinks include, but are not particularly limited to, solid foods such as dry foods containing orthosilicates and vitamins and minerals including the B vitamins—B1 (Thiamine), B2 (riboflavin), B6 and B12 (Cobalamin), vitamin E, Resveratrol, turmeric, Vitamin C, garlic, Calcium, wheat grass, and theanine, supplements, and liquid foods such as soft drinks or mineral water. Examples of solid foods include but are not limited to pasty products, processed soybean products, mousses, jellies, yogurt, frozen desserts, candy, chocolate, gum, crackers, biscuits, cookies, cakes, breads, and others. Liquids in which the composition can be provided in include but are not limited to teas, fruit and vegetable juice, carbonated drinks and milk. Current technology does not provide a composition that provides an increase metabolic rate of alcohol employing some of the aforementioned ingredients.

Accordingly, there is a need for a composition for increasing alcohol metabolism wherein the present invention is provided in a food substance and a drink formula both containing the composition of the present invention.

SUMMARY OF THE INVENTION

It is the object of the present invention to provide a composition that is operable to increase the metabolism of alcohol in a human wherein the composition of the present invention is provided is both a solid and a liquid form.

Another object of the present invention is to provide an alcohol metabolic rate increasing composition formulated to create a rise in the ability for a body to metabolize alcohol wherein the composition of the present invention includes B vitamins such as but not limited to thiamine, riboflavin, B6 and cobalamin.

A further object of the present invention is to provide a composition that is operable to increase the metabolism of alcohol in a human wherein the composition of the present invention further includes vitamin E, resveratrol and turmeric.

Still another object of the present invention is to provide an alcohol metabolic rate increasing composition formulated to create a rise in the ability for a body to metabolize alcohol wherein the composition of the present invention utilizes hydrous sodium aluminosilicate as the base for the composition.

An additional object of the present invention is to provide a composition that is operable to increase the metabolism of alcohol in a human wherein the composition of the present invention includes vitamin C, garlic, calcium, wheat grass and theanine.

Yet a further object of the present invention is to provide an alcohol metabolic rate increasing composition formulated to create a rise in the ability for a body to metabolize alcohol wherein alternate embodiments of the composition of the present invention further include calcium carbonate.

Another object of the present invention is to provide a composition that is operable to increase the metabolism of alcohol in a human wherein the alternate embodiments of the composition of the present invention include organic hemp powder and rhodiola extract.

Still an additional object of the present invention is to provide an alcohol metabolic rate increasing composition formulated to create a rise in the ability for a body to metabolize alcohol wherein the composition of the present invention alleviates or reduces disorders caused by ingestion of various alcoholic beverages and can be used spontaneously or on a daily basis.

Yet another object of the present invention is to provide a composition that is operable to increase the metabolism of alcohol in a human wherein the present invention can be ingested before, during or after ingesting an alcoholic beverage and subsequent ingestion the blood alcohol concentration in the body is reduced at a faster rate when compared to an unassisted rate.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

FIG. 1 is a table of elements of an embodiment of the present invention; and

FIG. 2 is a table of elements of an alternative embodiment of the present invention; and FIG. 3 is a table of elements of another embodiment of the present invention.

DETAILED DESCRIPTION

Referring now to the drawings submitted herewith, wherein various elements depicted therein are not necessarily drawn to scale and wherein through the views and figures like elements are referenced with identical reference numerals, there is illustrated an alcohol metabolism acceleration composition 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to the Figures submitted as a part hereof, the alcohol metabolism acceleration composition 100 in any form thereof includes a base. The base of the composition of the present invention is a hydrous sodium aluminosilicate. The hydrous sodium aluminosilicate has a clinoptilolite content that is at least ninety seven percent. While the preferred clinoptilolite content is at least ninety seven percent, it should be understood within the scope of the present invention that the clinoptilolite content could be as low as ninety percent. Furthermore, the preferred base of the composition of the present invention has a cation exchange capacity of one to two and a half micrograms per gram. The aforementioned base, hydrous sodium aluminosilicate, is employed in various media and serves as a base for the composition of the present invention for all of the embodiments discussed herein.

Multiple embodiments of the alcohol metabolism acceleration composition 100 are contemplated within the scope of the present invention and the Figures submitted herewith provide a breakdown of the preferred embodiments of the present invention. It should be understood within the scope of the present invention that the alcohol metabolism acceleration composition 100 could have further embodiments than the embodiments illustrated and discussed herein. Additionally, it should be further understood within the scope of the present invention that the percentages identified herein for the components of the alcohol metabolism acceleration composition 100 could vary from that preferred percentages and or weights discussed herein. Listed in FIG. 2 herein is an embodiment of the alcohol metabolism acceleration composition 100 contemplated within the scope of the present invention. The alcohol metabolism acceleration composition 100 of the embodiment of FIG. 2 includes four hundred milligrams of hemp protein powder. As is known in the art, hemp protein powder has a high content of omega 3 and omega 6 fatty acids. These fatty acids factor into the overall impact of this embodiment of the alcohol metabolism acceleration composition 100 due to the positive impact of the fatty acids on the cardiovascular health of the individual consuming this particular embodiment of the alcohol metabolism acceleration composition 100. The embodiment of FIG. 2 further includes two hundred and fifteen milligrams of rhodiola extract wherein the rhodiola extract contains two percent rosavin. Further included in this embodiment is magnesium wherein the magnesium is present at ninety seven milligrams. Vitamin B complexes are also present in the embodiment illustrated in FIG. 2 wherein both Vitamin B6 and B12 are included being present at levels of 32 milligrams and four micrograms respectively. Folic acid is also present at three hundred and eighty micrograms and further included is Vitamin D3 at four hundred international units (IU). Also present in the composition of the embodiment represented in FIG. 2 is silicon dioxide, magnesium stearate and microcrystalline cellulose. It should be understood within the scope of the present invention that the silicon dioxide is from processed clinoptilolite. The embodiment of the alcohol metabolism acceleration composition 100 illustrated in FIG. 2 is contemplated to be provided in both liquid and solid forms as well as suitable formats that can be combined with food.

Referring in particular to FIG. 1, an alternative embodiment of the alcohol metabolism acceleration composition 100 is illustrated therein. The embodiment outlined in FIG. 1 includes two hundred milligrams of silicon dioxide. It should be understood within the scope of the present invention that the silicon dioxide is from processed clinoptilolite. Further included in this embodiment of the alcohol metabolism acceleration composition 100 are absorbic acid at one hundred and fifteen milligrams as well as potassium sorbate at eighty milligrams. Vitamin B12 is present at the level within a range of one to two micrograms. Lastly, Vitamin D3 is present at two milligrams. It should be understood within the scope of the present invention that the embodiment of FIG. 1 could be provided in both liquid and solid forms.

Now referring to FIG. 3 submitted herewith, another embodiment of the alcohol metabolism acceleration composition 100 is listed therein. The embodiment of FIG. 3 includes five hundred milligrams of Vitamin C. Additionally included is five hundred milligrams of calcium carbonate. Magnesium oxide is present at one hundred milligrams. The alcohol metabolism acceleration composition 100 of FIG. 3 further includes ninety milligrams of a Vitamin B complex. Garlic powder is present at a level of three hundred milligrams. Lastly, an amount of ten milligrams of Vitamin E acetate is included in the alcohol metabolism acceleration composition 100 embodiment represented in FIG. 3. It is contemplated within the scope of the present invention that the embodiment presented in FIG. 3 could be provided in both liquid and solid forms. Examples of solid foods include pasty products, processed soybean products, mousses, jellies, yogurt, frozen desserts, candy, chocolate, gum, crackers, biscuits, cookies, cakes, breads. Liquid embodiment examples include but are not limited to teas such as green tea, oolong tea, black tea, herbal tea, concentrated juice, concentrated reduced juice, straight juice, fruit mixed juice, fruit juice with grains, fruit juice drinks, fruit and vegetable mixed juice, vegetable juices, carbonated drinks, soft drinks, milk drinks. The composition of the present invention is particularly preferably taken before, during, or after ingestion of a beverage containing alcohol.

The alcohol metabolism acceleration composition 100 further provides increased metabolic rates of alcohol within the human body by including some or all of the ensuing components to any of the embodiments of the alcohol metabolism acceleration composition 100 listed and discussed herein. The alcohol metabolism acceleration composition 100 can include by orthosilicates with the B vitamins, B1 (Thiamine) and B2 (riboflavin), vitamin E, Calcium, wheat grass, resveratrol, turmeric and theanine wherein the aforementioned are employed in micro-doses. Utilizing the foregoing in the embodiments of the alcohol metabolism acceleration composition 100 the body can be influenced to have the alcohol metabolism accelerate and also assist the body in burning the carbohydrates and sugars associated with alcohol consumption. The alcohol metabolism acceleration composition 100 rapidly reduces blood alcohol concentration by increasing ADH activity and ALDH activity. Dosage forms of the alcohol metabolism acceleration composition 100 can be provided by way of example but not limitation oral medicines, injections, patches, suppositories or inhalants. Oral medicines include conventionally used tablets, capsules, powders, granules and drinks. As described above, from the viewpoint of safety, there is no upper limit of the dose for and vitamins and minerals including the B vitamins—B1 (Thiamine), B2 (riboflavin), B6 and B12 (Cobalamin), vitamin E, Resveratrol, turmeric, Vitamin C, garlic, Calcium, wheat grass, and theanine. However, from an economic point of view and a viewpoint at the time of actual ingestion, the dose per dose of and vitamins and minerals including the B vitamins—B1 (Thiamine), B2 (riboflavin), B6 and B12 (Cobalamin), vitamin E, Resveratrol, turmeric, Vitamin C, garlic, Calcium, wheat grass, and theanine. The composition is dosed in a preferred dosage of 0.01 mg/kg body weight to 100 mg/kg body weight, preferably 0.1 mg/kg body weight to 80 mg/kg body weight and more preferably is between 0.1 mg/kg body weight and 50 mg/kg body weight.

A green tea extract can also be used in combination with the composition of the present invention. The green tea extract of the present invention contains catechins (A) in an amount of 0.001% to 90%, preferably 0.01% to 85%, and more preferably 0.1% to 80%. The catechins (A) contained in the green tea extract include non-epi-physical techins (B) such as catechin, gallocatechin, tetekin gallate, gallocatechin gallate, and epecatechin, epigallocatechin, epicatechin gallate. Epigallo is a general term for epkin physical techins (C) such as catechin gallate (that is, A=B+C). In addition, the composition of the catechins in the present invention further includes the weight ratio of the physical strength tekins (B) to the epi stamina tekins (C) is from 0.25 to 9.0, preferably from 0.43 to 9.0.

The composition of the present invention may further contain crude drugs, herbs, amino acids, vitamins, minerals, and other raw materials acceptable to foods. Here, the crude drug to be used is not particularly limited, but includes Rinokoso, Toki, Shakuyaku, Peony, Ginseng and the like. Herbs are not particularly limited, but include carrot seed, clove, coriander, cypress, cinnamon, juniper, ginger, sweet orange, no ginore, no chiyuri, bitter orange, fennel, black pepper, bay, pino mint, bergamot, mandarin, minorella, lemongrass, rosemary, gretz treasure, vanilla, hyssop, eucalyptus, lime, lemon, ylang ylang, cardamom, clari sage, jasmine, zeranium, benoregalia rose, rose, olibanum, potato beetle, zerayuum, sandalwood neroli, ichibena, petitdaren, betino ku, marjoram, melitzsa, rosewood and peppermint.

The alcohol metabolism promoting effect of the composition of the present invention is brought about by a decrease in blood alcohol concentration. That is, by taking the composition of the present invention before, during, or after ingesting an alcoholic beverage, the blood alcohol concentration based on the absorption of alcohol in the beverage into the body is reduced more quickly. Therefore, it is possible to alleviate or improve the disorder caused by the consumption of alcoholic beverages.

Within the scope of the present invention is a process to form and subsequently provide nano-capsules of some of the ingredients that are subsequently incorporated into various embodiments of the present invention. The process consists of packing nanoparticles of the desired nutrients such as vitamins, zeolites and other ingredients listed herein into a secondary shell to form nano-capsules. The small droplets required for nano-encapsulation, which is typically less than one hundred nanometers do not scatter light as do larger encapsulated materials. As such the nano-encapsulated materials are optically clear. The aforementioned clear emulsion enables the delivery of lipophilic flavors and bioactive compounds in otherwise color sensitive systems. Employing this method increases the functionality of the products and is further a characteristic particularly in demand by consumers. By encapsulating nutrients, it is ensured the product delivers those nutrients more effectively and further enhances the nutritional robustness of the product. Utilizing nano-encapsulation for vitamins, bioactive and other components of the present invention offers the aforementioned advantages over traditional processes. Nano-encapsulation increases bioavailability as well as shelf life. Vitamins are sensitive to degradation from conditions such as heat, light, oxygen and moisture, which is why the nano-encapsulation process incorporation of the present invention provides distinct advantages. The process prevents the deterioration of vitamins and other components and is further utilized for targeted delivery of some of the components of the present invention into the human intestinal system. In summary the nano-encapsulation process incorporates coating or trapping the vitamin or other component in another compound in the formula. Next a protective barrier is created which is operable to protects bioactive components. Ensuing creation of the protective barrier the vitamin or other component are incorporated into the final embodiment of the present invention utilizing suitable techniques.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A composition comprising:
    a base ingredient, wherein said base ingredient is hydrous sodium aluminosilicate;
    hemp protein powder, wherein said hemp protein powder is present at 400 milligrams;
    rhodiola extract, wherein the rhodiola extract contains two percent rosavin;
    at least two B vitamins, wherein the at least two B vitamins include B6 and B12;
    folic acid, wherein the folic acid is present at a level of 380 micrograms;
    magnesium, wherein said magnesium is present at 97 milligrams;
    silicon dioxide, wherein the silicon dioxide provided is from processed clinoptilolite;
    wherein the composition is provided in either a liquid or solid form and wherein the dosage of the composition is 0.01 mg/kg body weight to 100 mg/kg body weight and wherein the base ingredient, hemp protein powder, rhodiola extract and silicon dioxide and packed into secondary shells to form nanocapsules.

2. The composition as recited in claim 1, wherein the composition further includes at least one or more of the following selected from a group consisting of: orthosilicates, thiamine, riboflavin, vitamin E, calcium, wheat grass, resveratrol, turmeric or theanine.

3. The composition as recited in claim 2, and furthering including microcrystalline cellulose and magnesium stearate.

4. The composition as recited in claim 3, and further including vitamin D3, wherein the vitamin D3 is present at 400 IU.

5. The composition recited in claim 4, wherein the composition further includes at least one or more of the following selected from a group consisting of: herbs, amino acids or green tea extract.

\* \* \* \* \*